US007694568B2

(12) United States Patent
Hegen et al.

(10) Patent No.: US 7,694,568 B2
(45) Date of Patent: Apr. 13, 2010

(54) METHOD FOR THE NONDESTRUCTIVE MATERIAL TESTING OF HIGHLY PURE POLYCRYSTALLINE SILICON

(75) Inventors: Andreas Hegen, Burghausen (DE); Matthaeus Schantz, Reut (DE); Bruno Lichtenegger, Altoetting (DE)

(73) Assignee: Wacker Chemie AG, Munich (DE)

( * ) Notice: Subject to any disclaimer, the term of this patent is extended or adjusted under 35 U.S.C. 154(b) by 194 days.

(21) Appl. No.: 11/842,299

(22) Filed: Aug. 21, 2007

(65) Prior Publication Data

US 2008/0053232 A1    Mar. 6, 2008

(30) Foreign Application Priority Data

Aug. 30, 2006   (DE)   ........................ 10 2006 040 486

(51) Int. Cl.
*G01N 29/04*   (2006.01)
(52) U.S. Cl. ............................. 73/627; 73/618; 73/598; 73/600
(58) Field of Classification Search ........... 73/596–600, 73/614–616, 627–629, 618–625
See application file for complete search history.

(56) References Cited

U.S. PATENT DOCUMENTS

| 4,366,713 | A | * | 1/1983 | Gilmore et al. | ............... | 73/618 |
| 4,741,212 | A | * | 5/1988 | Rehwald | ...................... | 73/600 |
| 4,803,884 | A | | 2/1989 | Kaneta et al. | | |
| 5,289,949 | A | | 3/1994 | Gentile | | |
| 5,631,425 | A | * | 5/1997 | Wang et al. | ................... | 73/606 |
| 6,047,600 | A | | 4/2000 | Ottosson et al. | | |
| 6,089,095 | A | * | 7/2000 | Yang et al. | ..................... | 73/600 |
| 6,439,054 | B1 | | 8/2002 | Gore et al. | | |
| 6,865,948 | B1 | | 3/2005 | Chen | | |
| 6,941,811 | B2 | * | 9/2005 | Chen et al. | ..................... | 73/629 |
| 7,000,475 | B2 | * | 2/2006 | Oravecz et al. | ............... | 73/602 |
| 7,526,959 | B2 | * | 5/2009 | Kim et al. | ..................... | 73/628 |
| 2005/0028594 | A1 | | 2/2005 | Chen et al. | | |
| 2005/0257617 | A1 | * | 11/2005 | Busch et al. | .................. | 73/584 |
| 2008/0022774 | A1 | * | 1/2008 | Lu | ............................... | 73/606 |

FOREIGN PATENT DOCUMENTS

| DE | 102004022221 | 3/2006 |
| DE | 102005022729 | 11/2006 |
| JP | 6080169 | 3/1994 |
| JP | 2001-21543 | 1/2001 |
| JP | 2004149324 A | 5/2004 |
| JP | 2006010662 A | 1/2006 |

OTHER PUBLICATIONS

Rehwald et al., Non-Destructive Ultrasonic Detection of Thermoplastic Deformation in Silicon Wafers, Semicond. Sci. Technol., 1986, pp. 280-284, vol. 1.
Ostapenko et al., Crack Detection and Analyses Using Resonance Ultrasonic Vibrations in Crystalline Silicon Wafers, Photovoltaik Energy Conversion, pp. 920-923.

* cited by examiner

*Primary Examiner*—Helen C. Kwok
(74) *Attorney, Agent, or Firm*—Brooks Kushman P.C.

(57) ABSTRACT

Noncontaminating and nondestructive testing of a shaped polysilicon body for a material defect is accomplished by exposing the shaped polysilicon body to ultrasound waves, and the ultrasound waves are registered by an ultrasound receiver after they have passed through the shaped polysilicon body or reflected therein, so that material defects in the polysilicon are detected.

13 Claims, 2 Drawing Sheets

Fig. 1: Horizontal testing
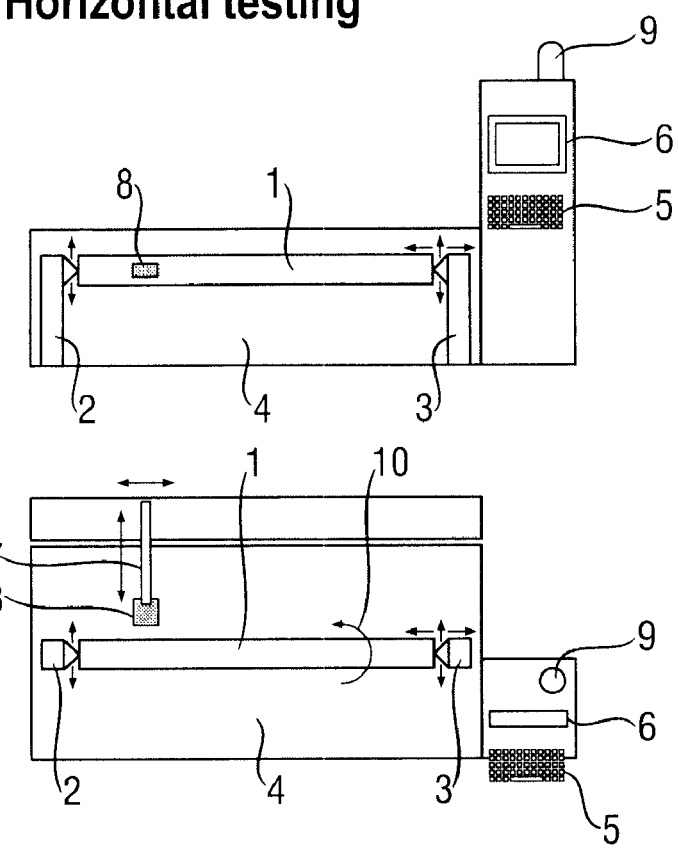
Fig. 2: Vertical testing
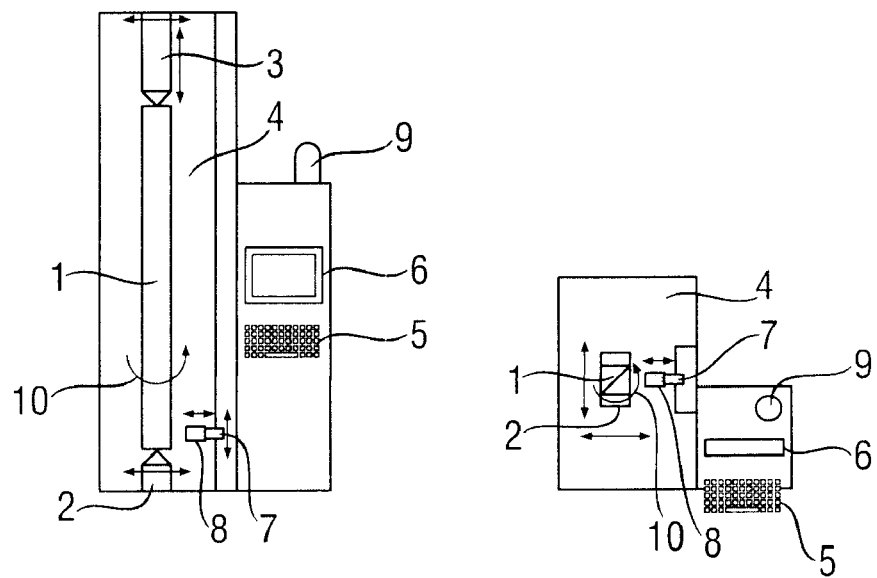

Fig. 3
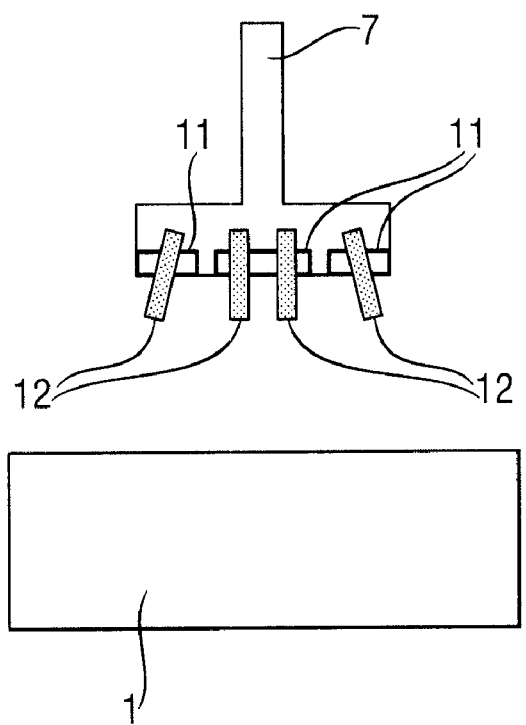
Fig. 4
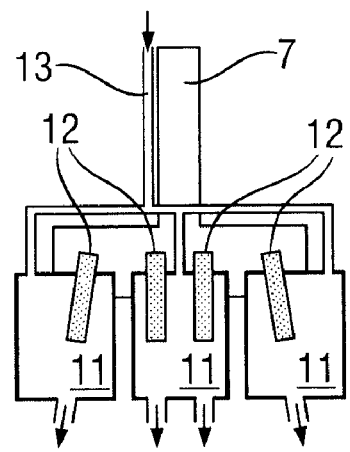
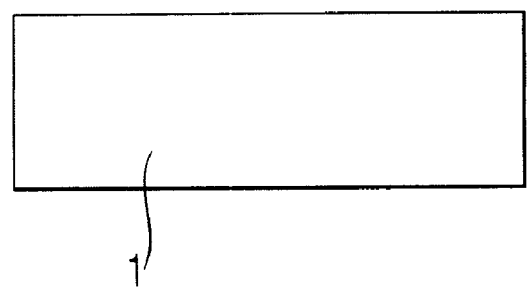

METHOD FOR THE NONDESTRUCTIVE MATERIAL TESTING OF HIGHLY PURE POLYCRYSTALLINE SILICON

BACKGROUND OF THE INVENTION

1. Field of the Invention

The invention relates to a method for the nondestructive material testing of highly pure polycrystalline silicon.

2. Background Art

Highly pure polycrystalline silicon, referred to below as polysilicon, is used inter alia as a starting material for the production of electronic components and solar cells. It is produced on an industrial scale by thermal decomposition and CVD deposition of a gas containing silicon or a gas mixture containing silicon in Siemens reactors. The polysilicon is in this case formed as shaped polysilicon bodies. These can subsequently be processed mechanically.

These shaped polysilicon bodies must be tested by means of a nondestructive test method to assess their material quality. Acoustic resonance analysis, also known as a "sound test", is generally used for this. The shaped polysilicon body is externally excited, for example by a gentle hammer blow, and the natural resonances resulting from this provide the person skilled in the art with information about the material quality of the shaped polysilicon body. One advantage of resonance is the very short test time of only a few seconds. The entire specimen body is furthermore studied during the test, i.e. the test is a volume-oriented test method. A disadvantage of resonance analysis is that accurate localization or material defect identification is not possible with this method. Moreover, the shaped polysilicon body is touched by a hammer blow and therefore contaminated in each test, which necessitates a subsequent cleaning step. Another disadvantage of resonance analysis is that the shaped polysilicon body may be damaged by the test. For example, superficial dislocations or even destruction of the shaped polysilicon body may take place. A further disadvantage is that the shaped polysilicon bodies differ in their shape, for example in diameter and length or in length, width and height or finished article geometry, and each shaped polysilicon body generates a different natural resonance owing to its different geometry. This makes comparison of the test results more difficult. Small defects which compromise the material quality, such as cracks, cavities or inclusions whose dimension is only a few millimeters large, cannot be detected by this test method.

Visual inspection is another nondestructive test method for polysilicon. The entire surface of the shaped polysilicon body to be tested is in this case assessed by a person skilled in the art. Visual inspection can be improved by various aids, such a special illumination systems or magnifying glasses. Although surface defects can also be identified and localized by visual inspection, here again material defects inside the shaped polysilicon bodies disadvantageously cannot be identified. The test is furthermore carried out by a person, i.e. the results are not objective and reliably reproducible; rather, they depend on the tester's "daily form" and experience.

For both said nondestructive test methods, furthermore, the shaped polysilicon body is handled with aids by the user. These aids, for example gloves, may become laden with dirt particles between two tests, which leads to contamination of the shaped polysilicon body during the test and necessitates a subsequent cleaning step.

SUMMARY OF THE INVENTION

It was an object of the invention to provide a nondestructive test method for a shaped polycrystalline silicon body to assess material defects, which does not have the disadvantages mentioned for the prior art. These and other objects are achieved by a method in which the shaped polycrystalline silicon body is exposed to ultrasound waves and the ultrasound waves are registered by an ultrasound receiver after they have passed through the shaped polysilicon body, so that material defects in the polysilicon are detected.

BRIEF DESCRIPTION OF THE DRAWINGS

FIG. 1 illustrates a device for horizontal testing by means of one embodiment of a method according to the invention in a side view and plan view;

FIG. 2 illustrates a device for vertical testing by means of one embodiment of a method according to the invention in a side view and plan view. The numbering corresponds to FIG. 1;

FIG. 3 illustrates one embodiment of a test head unit (8) on a scanning arm (7) consisting of test head holders (11) and ultrasound test heads (12) for underwater testing, as described for example in Ex. 1; and FIG. 4 illustrates one embodiment of a test head unit (8) on a scanning arm (7) consisting of the test head holders (11) and the ultrasound test heads (12) for water jet testing, as described for example in Ex. 2.

DETAILED DESCRIPTION OF THE PREFERRED EMBODIMENT(S)

According to the invention, ultrasound waves in the frequency range of from 100 kHz to 25 MHz, more preferably from 0.8 MHz to 20 MHz, and especially 2-12 MHz, are introduced by an ultrasound test head into the polycrystalline silicon. They propagate in a straight line in the polysilicon, but are reflected at interfaces such as those found at material defects (for example cracks, cavities or inclusions) but also at the transition from polycrystalline silicon to air. The material defects can be located best when their main dimension extends perpendicularly to the propagation direction of the ultrasound waves in the polysilicon. The shaped polysilicon body is therefore preferably irradiated from all sides in the course of the method according to the invention, since accurate noncontaminating and nondestructive identification of the position of the detected material defect in the shaped polysilicon body is thereby possible.

The shaped polysilicon body may be irradiated by means of the acoustic transmission method or by means of the pulse-echo method, the latter being preferred.

In the acoustic transmission method, the polycrystalline silicon is arranged between an ultrasound emitter and an ultrasound receiver. The ultrasound waves having passed through the polysilicon are converted back into electrical oscillations (piezo effect) by an ultrasound receiver and are displayed. Owing to its interface with the polysilicon, a material defect is manifested by a reduced or missing signal. Depth determination of a defect is not possible with this method. Although this variant of ultrasound measurement is usable in principle, the pulse-echo method as described below is nevertheless preferably employed according to the invention.

Except the comments about the depth determination and defect evaluation of a defect, however, the following comments about the pulse-echo method also apply similarly for the acoustic transmission method.

In the pulse-echo method, the ultrasound test head is used as an emitter and receiver for the ultrasound waves. A sound pulse, which lies in the frequency range of from 100 kHz to 25 MHz, more preferably from 0.8 MHz to 20 MHz, and especially 2-12 MHz, is radiated into the shaped polysilicon body by the ultrasound test head, registered by the same ultrasound test head after complete or partial reflection and converted back into a receiver pulse. The emitted pulse, backwall echo and possibly defect echo(es) are registered electronically, depth determination of a material defect being possible using the respective time of flight of the reflected ultrasound waves. Any echo which occurs in the defect expectation range, i.e. the range between the surface echo and the backwall echo, is then preferably categorized as a defect echo. The registered sound pulses are preferably output in dB (logarithm to the base 10).

In the method according to the invention, preferably from 1 to 5 ultrasound test heads are integrated in a test head holder. The ultrasound test heads and the corresponding test head holder will be referred to below as a test head unit. Angled test heads with incidence angles of between 10° and 85° in the silicon or perpendicular test heads are preferably used.

The test head unit is preferably moved up to the shaped polysilicon body. To this end, the test head unit is preferably provided with a contactless spacer. The test head distance is preferably from 5 to 200 mm, more preferably from 5 to 80 mm.

Utrasound coupling has been carried out with gel, oil, paste or water. Owing to the high material purity of the polysilicon, only water can be used according to the invention as a coupling medium for polysilicon.

Tests have shown that the following surface metal values are to be found on the polysilicon surface after testing with drinking water as a coupling medium:

surface of the shaped polysilicon body remaining highly pure (surface metal values: $Fe \leq 15$; $Cr \leq 1$; $Ni \leq 0.5$; $Na \leq 25$; $Zn \leq 10$; $Cl \leq 30$; $Cu \leq 1$; $Mo \leq 1$; $Ti \leq 25$; $W \leq 1$; $K \leq 5$; $Co \leq 0.5$; $Mn \leq 0.5$; $Ca \leq 45$; $Mg \leq 11$; $V \leq 0.5$; all specifications are in pptw).

The ultrasound coupling may be carried out by a water jet technique or by an immersion technique. With the water jet technique, the ultrasound coupling is preferably carried out by means of a water jet which joins the ultrasound test head to the surface of the shaped polysilicon body freely from air bubbles. With the immersion technique, the entire test takes place under water so that the ultrasound test head is likewise joined bubble-free to the surface of the test body.

After the ultrasound coupling, the exposure of the shaped polysilicon body to the ultrasound waves begins. The shaped polysilicon body is preferably monitored by the ultrasound test head during the test. The monitoring is carried out in any way, more preferably in the direction of the longitudinal axis of the shaped body to be tested, most particularly preferably in a lateral direction along the longitudinal axis and the circumference of the shaped body to be tested. Simultaneously or alternatively, the shaped polysilicon body itself may be moved, for example lowered, raised or moved horizontally. The shaped polysilicon body itself may also be set in rotation.

The monitoring/test rate preferably lies between 1 and 1500 mm/s, more preferably between 150 mm/s and 600 mm/s.

The signal evaluation of the reflected ultrasound waves is preferably carried out in a computation instrument. In this case the signal of the reflected ultrasound waves in a defined time window, the so-called defect expectation range, is compared in the computation device with a base noise level or a defined signal threshold value. If the base noise level or the defined signal threshold value is exceeded, then the shaped polysilicon body is categorized as defective and assigned to the defective subset (shaped polysilicon body not ok). By varying the signal threshold value, the sensitivity of the defect identification can be varied continuously.

| Fe | Cr | Ni | Na | Zn | Cl | Cu | Mo | Ti | W | K | Co | Mn | Ca | Mg | V |
|---|---|---|---|---|---|---|---|---|---|---|---|---|---|---|---|
| 1500 | 100 | 50 | 2500 | 100 | 300 | 50 | 1 | 250 | 1 | 500 | 0.5 | 15 | 4500 | 1500 | 0.5 |

All specifications are in pptw. The effect of this is that all the tested material must subsequently also be cleaned.

Surprisingly, the ultrasound coupling can also be carried out by means of bubble-free, fully deionized water. Tests have shown that the following surface metal values are to be found on the polysilicon surface after testing with fully deionized water ($pH \leq 7.0$; resistance=18 megOhm; free of suspended matter) as a coupling medium:

The result is in this case preferably output by means of a display device which outputs an unambiguous result, generally "shaped polysilicon body ok" or "shaped polysilicon body not ok". The test parameters, such as the defined signal threshold value, start of the defect expectation range, end of the defect expectation range, are preferably stored in the form of test programs in the computation unit so that the method can be adapted rapidly and simply to various defect limits for

| Fe | Cr | Ni | Na | Zn | Cl | Cu | Mo | Ti | W | K | Co | Mn | Ca | Mg | V |
|---|---|---|---|---|---|---|---|---|---|---|---|---|---|---|---|
| 15 | 1 | 0.5 | 25 | 10 | 30 | 1 | 1 | 25 | 1 | 5 | 0.5 | 0.5 | 45 | 11 | 0.5 |

All specifications are in pptw. By using fully deionized water, it is thus possible to obviate subsequent recleaning of the shaped polysilicon body.

The method according to the invention thus for the first time makes it possible to test a shaped polysilicon body, the different dimensions and quality changes, depending on the geometry and intended purpose of the shaped polysilicon body. Furthermore, as described, the computation instrument makes it possible to determine the position of the defect in the shaped polysilicon body and thus specify defective regions in the shaped polysilicon body. To this end, the shaped silicon body with the defective and defect-free regions may be represented on the result output.

After the ultrasound test, the shaped polysilicon is preferably dried, preferably by a nozzle supplied with compressed air which travels along the test path in the opposite direction to the test, until the specimen is dried.

The shaped polysilicon body preferably comprises polysilicon rods or rod pieces. The shaped polysilicon body preferably has a diameter of from 3 mm to 300 mm, more preferably a diameter of from 50 mm to 200 mm. The length of the shaped body is in principle unrestricted, shaped bodies with a length of from 10 mm to 4500 mm capable of being analyzed, in particular from 100 mm to 3000 mm, preferably being tested. The shaped bodies are preferably provided with a machine-readable identity (ID) number, which makes it possible to record the shaped body with the aid of the ID number in the method according to the invention. This may, for example, be done using the computation instrument.

The method is suitable for testing shaped polysilicon bodies of any geometry. For example, even a banana-shaped body may be tested. The method furthermore permits nondestructive material testing of highly pure silicon. Concealed material defects in the surface vicinity and inside the material are detected. The method delivers an unambiguous and reproducible test result. When using the pulse-echo method, the material defects can also be accurately localized and identified inside the polysilicon.

The method operates freely from contamination. The shaped polysilicon body to be tested comes in contact only with the aid, i.e. water, preferably with fully deionized water (pH$\leq$7.0; resistance$\geq$0.5 megOhm, more preferably resistance$\geq$18 megOhm; free of suspended matter). Preferably, this aid required for the test is continuously tested qualitatively to 100%, since the quality of this aid has a direct effect on the surface metal values of the shaped polysilicon body.

The method is a volume-oriented test method, i.e. material defects from a few tenths of a millimeter to millimeters can be detected and localized accurately throughout the shaped polysilicon body. Thus, even defects with a diameter of 0.2 mm at a depth of 130 mm could be detected in a shaped polycrystalline polysilicon body by means of the method according to the invention. Conversely, only material defects in the range of centimeters to decimeters lying in the bulk can be detected by means of resonance analysis. Visual inspection allows only surface-oriented testing, i.e. only visible surface defects can be detected.

The automated test method of the invention excludes error-prone subjective assessment by a person, and it does not overlook any defects. The test method delivers an unambiguous and reproducible test result (specimen—OK/specimen—not OK), and it furthermore makes it possible to define specification noncompliant regions of a shaped polysilicon body. The method does not need any special preparation of the shaped polysilicon body to be tested, so that it can be incorporated simply into an existing fabrication process. For example, cylindrical and conical shaped polysilicon bodies for an FZ refining process can be inspected for material defects by the method. Rods or rod pieces (for example cut rods, rebatch rods etc.) for an FZ or CZ refining process can furthermore be studied for material defects.

The invention thus for the first time provides a shaped polysilicon body that contains no defects, which are preferably intended to mean cracks, cavities or inclusions with a projection surface larger than 0.03 mm$^2$. A shaped polysilicon body according to the invention preferably contains no defects at all and exhibits a reduced cleaving and flaking behavior during the subsequent melting and refining processes.

Two embodiments of the method according to the invention are schematically represented in FIGS. 1 and 2.

The following examples serve to explain the invention further.

EXAMPLE 1

Horizontal Testing Under Water

A shaped polysilicon body (1) with a diameter of 200 mm and a rod length of 2500 mm is tested horizontally in a device according to FIG. 1 under water. To this end the shaped polysilicon body (1) is arranged horizontally in the water reception trough (4) and clamped between the tips of the specimen retainers (2) and (3). The water reception trough (4) is filled with fully deionized water. In parallel with this, the shaped silicon body (1) provided with a machine-readable identity (ID) number is registered with the computation instrument (5+6), i.e. the machine-readable identity (ID) number is communicated to the computation instrument (5+6). The test program stored in the computer instrument is subsequently selected and the test is started.

The scanning arm (7), at the end of which the ultrasound test head unit (8) is fastened, moves with a rate of advance of 10 mm/s in the direction of the shaped polysilicon body (1). When the ultrasound test head unit (8) reaches a distance of 5 mm between the ultrasound test head unit (8) and the shaped polysilicon body (1), the advance of the scanning arm (7) is set.

The ultrasound test head unit (8) consists of 3 test head holders (11), 4 ultrasound test heads (12) (FIG. 3) and the contactless distance electronics, which are integrated in the scanning arm (7) (not depicted) and keep the distance between the test head holders and the shaped body constant.

The ultrasound test heads (12) are operated using the pulse-echo method. Each ultrasound test head (12) emits pulses with a frequency of 12 MHz in a definitively preset sequence and receives the reflected signals. The scanning arm (7) moves at a constant speed of 1200 mm/s from the specimen retainer (2) to the specimen retainer (3) along the surface of the shaped polysilicon body (1).

The shaped polysilicon body (1) is rotated through 1 mm in the circumferential direction by means of the specimen retainers (2) and (3). The scanning arm (7) moves back at 1200 mm/s from the specimen retainer (3) to the specimen retainer (2) along the surface of the shaped polysilicon body (1). The received signals are evaluated in parallel with this in the computation instrument (5+6) and the results are visualized. If a material defect is discovered, then a light (9) flashes until the end of the test. The described procedure is continued with the shaped polysilicon body (1) until the entire circumference of the shaped polysilicon body has been scanned and therefore tested. After the end of the test, the fully deionized water is discharged from the water reception trough (4). The specimen retainers (2) and (3) are opened and the shaped polysilicon body (1) is removed from the measuring device. Depending on the display (9), the shaped polysilicon body (1) is categorized as defect-free or defective.

EXAMPLE 2

Horizontal Testing with Water Jet Coupling

A shaped polysilicon body (1) with a diameter of 200 mm and a rod length of 2500 mm is tested horizontally according to FIG. 1 with water jet coupling. The test procedure is carried out similarly as Example 1, with the difference that the water reception trough (4) is not filled with fully deionized water during the ultrasound testing and the ultrasound test head unit (8) is constructed as represented in FIG. 4 and as described below:

The ultrasound test head unit (8) consists of 3 test head holders (11), 4 ultrasound test heads (12) and the contactless distance electronics (not depicted), which are integrated in the scanning arm (7) and keep the distance between the ultrasound test head unit (8) and the shaped polysilicon body (1) constant. Fully deionized water is supplied continuously to the test head holders (11) via lines (13). This water fills the space around the ultrasound test heads (12) and forms a water jet, which provides the ultrasound coupling between the ultrasound test heads (12) and the surface of the shaped polysilicon body (1). The test is carried out as described in Ex. 1.

Following the test run, but in the opposite direction, the shaped polysilicon body (1) is dried by means of compressed air (not shown). After the shaped polysilicon body (1) has been dried, the tips of the specimen retainers (2) and (3) are opened and the shaped polysilicon body (1) is removed. Depending on the display (9), the shaped polysilicon body (1) is categorized as defect-free or defective.

EXAMPLE 3

Vertical Testing Under Water

The test is carried out similarly to Example 1 by using the ultrasound test head unit represented in FIG. 3, with the difference that the shaped polysilicon body (1) is tested vertically as represented in FIG. 2.

EXAMPLE 4

Vertical Testing with Water Jet Coupling

The test is carried out similarly to Example 2 by using the ultrasound test head unit represented in FIG. 4, with the difference that the shaped polysilicon body (1) is tested vertically as represented in FIG. 2.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for a noncontaminating and nondestructive testing for material defects of a polysilicon rod having a surface and having a diameter of from 3 mm to 300 mm and a length of 10 mm to 4500 mm, formed by CVD deposition of silicon in Siemens process, wherein the polysilicon rod or a portion thereof is exposed to ultrasound waves transmitted by an ultrasound transmitter and reflected ultrasound waves are received by an ultrasound receiver after the waves have passed through the polysilicon rod, such that material defects in the polysilicon rod are detected, ultrasound coupling being maintained between the rod and an ultrasound transmitter and an ultrasound receiver by a water jet technique in bubble-free deionized water.

2. The method of claim 1, wherein the ultrasound waves are radiated through the polysilicon rod by the ultrasound transmitter and the ultrasound waves having passed through the polysilicon rod are converted back into electrical oscillations by the ultrasound receiver and are displayed.

3. The method of claim 1, wherein the ultrasound waves are radiated through the polysilicon rod by an ultrasound test head and, having been received by the same ultrasound test head after complete or partial reflection, are converted back into a receiver pulse.

4. The method of claim 1, wherein the transmitted and received ultrasound waves are electronically received and evaluated, a position determination of the material defect in the polysilicon rod being carried out using the respective time of flight of the ultrasound waves.

5. The method of claim 3, wherein the ultrasound test head is moved up to the polysilicon rod and coupled to the polysilicon rod by means of ultrasound coupling, before exposure to the ultrasound waves takes place.

6. The method of claim 4, wherein the evaluation of the electronically received reflected ultrasound waves is carried out in a computation instrument, the time differences between the reflected ultrasound waves, the signal strength between the reflected ultrasound waves, or both the time differences and the signal strength between the reflected ultrasound waves being compared with predetermined parameters in the computation instrument.

7. The method of claim 3, wherein the ultrasound test head is moved up to a test head distance of from 5 to 200 mm from the polysilicon rod.

8. The method of claim 3, wherein the ultrasound test head is moved up to a test head distance of from 5 to 80 mm from the polysilicon rod.

9. The method of claim 1, wherein the water is fully deionized (pH$\leq$7.0; resistance$\geq$0.5 megOhm).

10. The method of claim 1, wherein the water is fully deionized (pH$\leq$7.0; resistance$\geq$18 megOhm).

11. The method of claim 1, wherein the surface of the polysilicon rod remains highly pure, with surface metal values: Fe$\leq$15; Cr$\leq$1; Ni$\leq$0.5; Na$\leq$25; Zn$\leq$10; Cl$\leq$30; Cu$\leq$1; Mo$\leq$1; Ti$\leq$25; W$\leq$1; K$\leq$5; Co$\leq$0.5; Mn $\leq$0.5; Ca$\leq$45; Mg$\leq$11; V$\leq$0.5; (all specifications in pptw).

12. The method of claim 1, wherein the polysilicon rod contains no undetectable defects which are larger than 0.03 mm$^2$ in projection surface.

13. A polysilicon rod which contains no defects with a projection surface larger than 0.03 mm$^2$, as determined by the method of claim 1.

* * * * *

UNITED STATES PATENT AND TRADEMARK OFFICE
CERTIFICATE OF CORRECTION

| | |
|---|---|
| PATENT NO. | : 7,694,568 B2 |
| APPLICATION NO. | : 11/842299 |
| DATED | : April 13, 2010 |
| INVENTOR(S) | : Andreas Hegen et al. |

Page 1 of 1

It is certified that error appears in the above-identified patent and that said Letters Patent is hereby corrected as shown below:

Column 7, Line 55, Claim 1:

After "silicon in" and before "Siemens" insert -- a --.

Signed and Sealed this

Twenty-second Day of June, 2010

David J. Kappos
*Director of the United States Patent and Trademark Office*